United States Patent [19]

Hermann

[11] Patent Number: 5,020,908
[45] Date of Patent: Jun. 4, 1991

[54] APPARATUS FOR THE OPTICAL DETECTION OF FLAWS, IN PARTICULAR CRACKS IN TRANSPARENT OBJECTS

[76] Inventor: Peter Hermann, Haldenstrasse 33, 2555 Brügg/Biel, Switzerland

[21] Appl. No.: 503,131

[22] Filed: Mar. 30, 1990

Related U.S. Application Data

[63] Continuation of Ser. No. 931,519, Nov. 14, 1986, abandoned.

[30] Foreign Application Priority Data

Nov. 15, 1985 [EP] European Pat. Off. ......... 85810544.8

[51] Int. Cl.$^5$ .............................................. G01N 21/90
[52] U.S. Cl. .................................... 356/239; 356/240; 250/223 B
[58] Field of Search ............... 356/239, 240, 237, 428; 250/223 B; 209/526

[56] References Cited

U.S. PATENT DOCUMENTS

| | | | |
|---|---|---|---|
| 4,201,338 | 5/1980 | Keller | 356/240 |
| 4,208,130 | 6/1980 | Saconney et al. | 356/240 |
| 4,293,219 | 8/1978 | Ducloux | 356/240 |

FOREIGN PATENT DOCUMENTS

| | | |
|---|---|---|
| 0061021 | 3/1981 | European Pat. Off. |
| 2940122 | 10/1978 | Fed. Rep. of Germany |
| 8103706 | 6/1981 | Fed. Rep. of Germany |
| 2378276 | 1/1977 | France |
| 2432342 | 8/1978 | France |

*Primary Examiner*—Samuel Turner
*Attorney, Agent, or Firm*—Marks, Murase & White

[57] ABSTRACT

An apparatus for the optical detection of cracks in transparent objects having several radiation sources and several groups of detectors which each have eight detectors. Each radiation impulse from one or more radiation sources may impinge on one or more groups of detectors and form an electro-optical channel independent of the others. The channels are switched on and off periodically one after the other. The sensitivity level of each group of detectors is individually programmable. The groups of detectors and the radiation sources are mounted on a stand so that they may be adjusted having a frame with holders. Light scattering is minimized by fitting the groups of detectors with shields. Such an apparatus can be relatively simply set up and adjusted and be simplified as a result of the separation of the electro-optical channels. The electronic switching permits a rapid, safe and automatic detection of flaws when a suitable microprocessor is employed.

24 Claims, 7 Drawing Sheets

APPARATUS FOR THE OPTICAL DETECTION OF FLAWS, IN PARTICULAR CRACKS IN TRANSPARENT OBJECTS

This application is a continuation, of application Ser. No. 06/931,519, filed 11-14-86, now abandoned.

BACKGROUND OF THE INVENTION

The instant invention relates to an apparatus for the detection of flaws, in particular cracks, in transparent objects by optical means, having a plurality of radiation sources, having a plurality of detectors associated therewith, which form channels and with evaluation means for the display or the flaws whereby means are provided for the sequential and periodic switching of the channels and for preventing the individual channels from disturbing each other. Such an apparatus is described in our specification No. WO-A-81/03706 and relates in particular to the testing of hollow glass objects for cracks and other flaws. This testing for cracks is based on total reflection, whereby cracks in hollow glass vessels may occur in all parts of the vessel such as the opening, shoulder, body and base and may, in addition, be unevenly distributed. Cracks may occur horizontally as well as vertically and as distorted cracked surfaces. The main orientation of a crack can be defined by two angles. The apparatus in the specification takes the various different types of cracks into account and permits measurements to be carried out according to a multiplex process. Such an apparatus does, however, display certain disadvantages. For example, in each detector group o/nly one diode is active, depending on the channel. This has the result that detection is not perfect in the vertical area and that narrow bundles of light from cracks may rot, or not completely, be detected. The above described apparatus furthermore requires a large number of electric leads to the digital analog converter.

OBJECT OF THE INVENTION

It is therefore an object of the instant invention to provide a detection apparatus which is of simple construction and thereby a more rapid and secure measurement of flaws as well as a comprehensive evaluation and recording of flaws statistics.

SUMMARY OF THE INVENTION

The instant invention relates to an apparatus for the detection of flaws, in particular cracks, in transparent objects, by optical means, comprising a plurality of radiation sources having a plurality of detectors associated therewith, forming independent electro-optical channels and having evaluation means for the evaluation of flaws, whereby switching means are present for switching the channels sequentially and periodically, whereby the individual detectors are arranged together in small strip-like detector groups, whereby the sensitivity level can be independently adjusted and whereby the groups of detectors and also the radiation sources are adjustably secured to a stand having a frame provided with holders.

The detectors are preferably provided with means for reducing scattered light such as shields mounted on the detector housings or roughened, blackened surfaces, positioned between the shields and the receiving diode. The detectors are conveniently provided with a lens, in particular a cylindrical lens which may also have roughened and blackened sides which focus the impinging light on the receiving diode.

The radiation sources may each be provided with an optical system, comprising a glass fibre and piece having variable cross-section leading into a glass fibre conductor, having a shielding tube with a lens arranged therein, an interchangeable image diaphragm, means for deflecting the radiation, such as a double wedge, a prism or a deflecting mirror and a shield, whereby said radiation sources are disposed parallel to each other on a stand. The radiation source may be an inert gas discharge tube in particular a xenon tube having a filamentary arc. The radiation source may be a light emitting diode, a laser diode, a laser emitter or a mixed light source.

A plurality of groups of detectors may conveniently be assembled together in units at given levels which may be adjusted vertically in a grid pattern and horizontally in the direction the object being measured.

A plurality of groups of detectors may also furthermore be employed arranged in layers in a semicircular holder whereby each holder is mounted in a vertically adjustable manner in a frame, whereby for each holder not more than one electrical connection is required for the detectors and optionally the light sources.

The electronic control system may be provided with a control and evaluation unit having a microprocessor, which on the one hand receives a signal from the different sensors of the testing installation and on the other hand controls the various drive parts of the installation as well as the inspection unit, in which the various operating elements of the measuring apparatus can be displayed and is connected to a radiation source switching control and a detector group switch. Between the control and evaluation units and the inspection unit a memory interface may be incorporated in which all measuring information from a glass can be intermittently stored. Each group of detectors may comprise eight detectors and a switch, whereby each detector is provided with an impulse amplifier having direct current suppression and a comparator and four comparators are connected to each OR gate, from which the signal proceeds to an AND gate, in which the signal is compared with a level memory, whereby the level memory is programmable and connected via a digital analog converter and an adaptor to the negative terminals of the comparator.

The control unit of the apparatus may conveniently have a front panel having arranged thereon a display from a given group of detectors, display elements for crack displays in certain groups of detectors and keys for programming the levels in the groups of detectors, whereby the display and the choice of a chosen channel is independent, as well as a detector level display board having a delete key and a channel display and programming field in which a given channel is programmed and displayed and it is also displayed in which channel of the group of detectors flaw conditions prevail. The front panel preferably has a sum total crack display (CH) and the control unit has a counter for each channel.

The instant invention also provides a light source for measuring systems, in particular for the detection of flaws in transparent objects having an inert gas discharge tube connected to a direct current source and which may be ignited by a high tension impulse, wherein an electrically conducting ignition mirror is connected to an ignition transformer in parallel to the discharge tube.

The instant invention also provides a switching circuit comprising a lamp control diode for collecting the light yield which is connected to a regulator and with the lamp logic as well as an auxiliary device for the detection of flaws in transparent objects, comprising a screen and a radiation source mounted on a stand.

BRIEF DESCRIPTION OF THE DRAWINGS

One particular embodiment which is in accordance with these objects is now described hereinafter together with the drawings appended hereto.

DETAILED DESCRIPTION OF THE INVENTION

Figure 1:
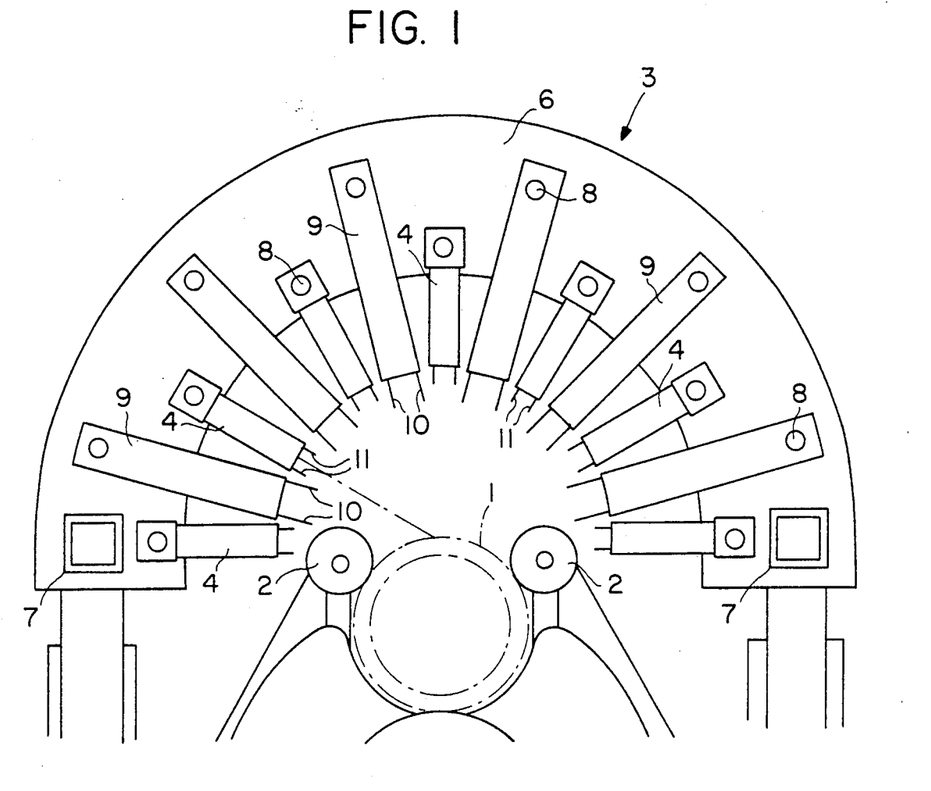
FIG. 1 shows a schematic plan view of an apparatus according to the instant invention.
Figure 2:
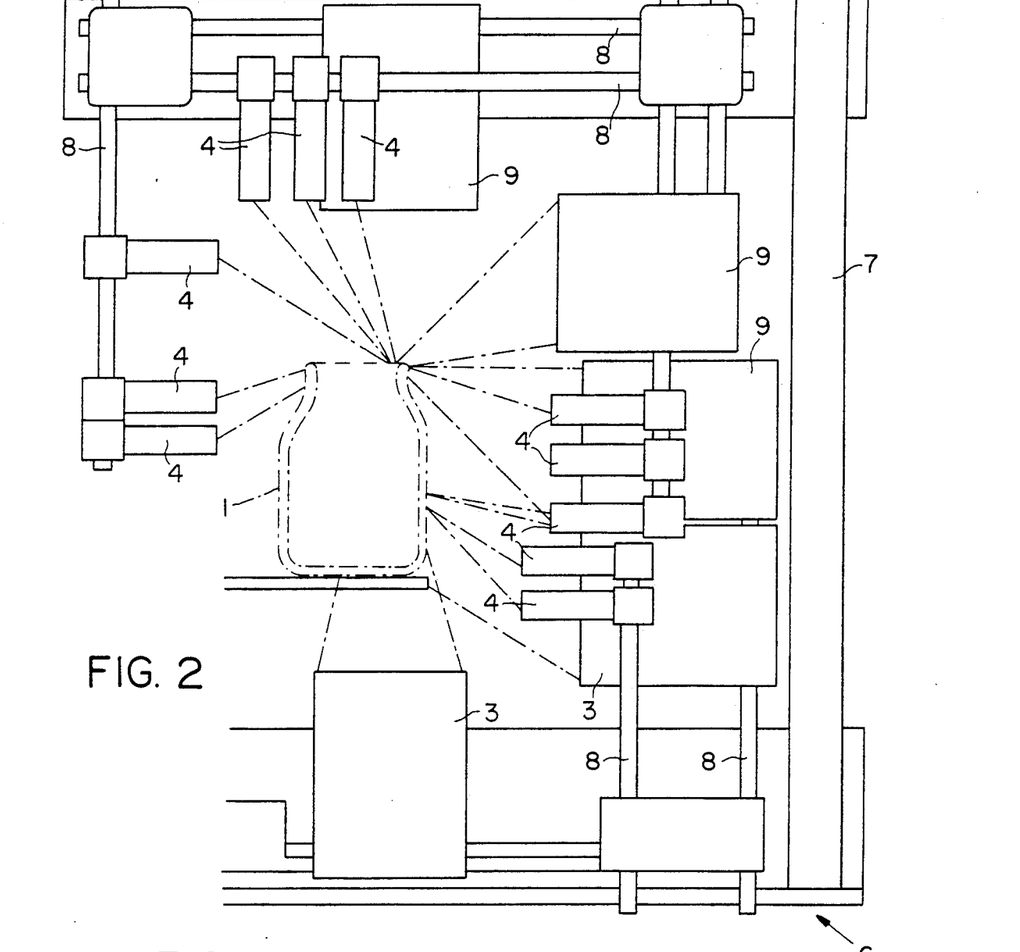
FIG. 2 shows a side view of the apparatus of FIG. 1.

FIGS. 1 and 2 show the object being mesured 1, a bottle which stands on a transport system not further herein described, which is rotated about its axis by means of two rollers 2. The optical arrangement 3 comprises light sources 4 and detectors 5 which are disposed in a semi-circle around the surface of the object being measured. The entire optical arrangement is mounted on a stand 6. This stand 6 comprises a frame 7 to which the light sources and the detectors are fixed by means of holders 8 so as to be horizontally or vertically moveable and adjustable. As shown in particular in FIG. 2, the detectors are arranged in detector groups 9 and are generally left in a given disposition since their position is, in principle, not critical. In the present example the detector groups are arranged in two levels of six groups each. The light sources, in turn, are arranged in groups of different size and adjusted to the object to be measured and to the ranges to be measured. So that as little scattered light as possible reaches the detectors, these are equipped with shields 10. Similarly the light sources have shields 11 in order to keep the amount of disturbing light or of direct light as low as possible.

Figure 6:
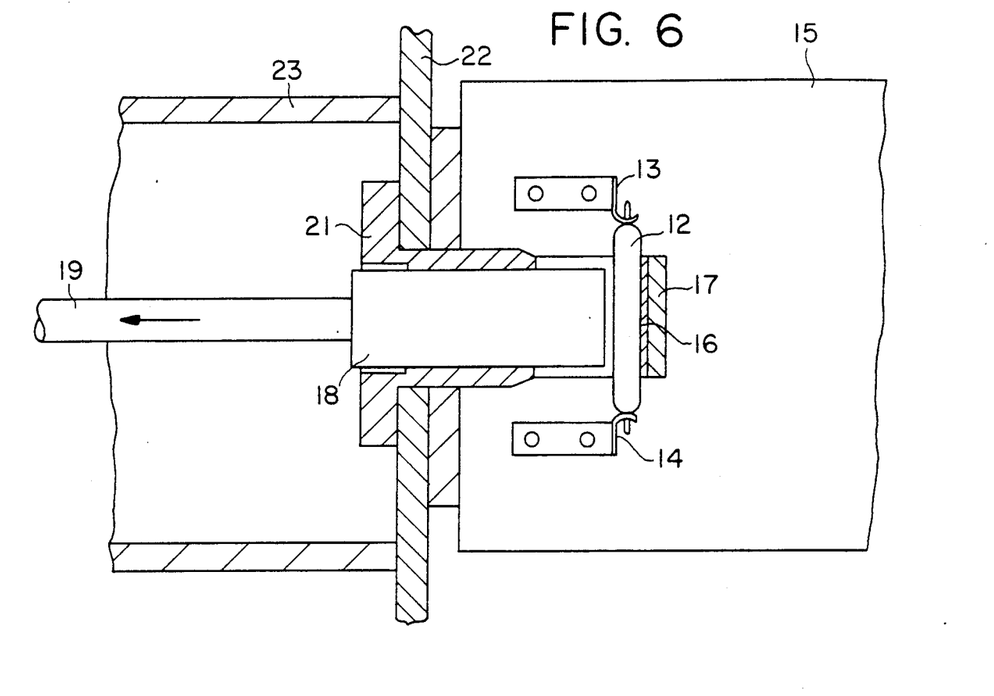
FIG. 6 shows a longitudinal cross-section of the construction of a light source
Figure 7:
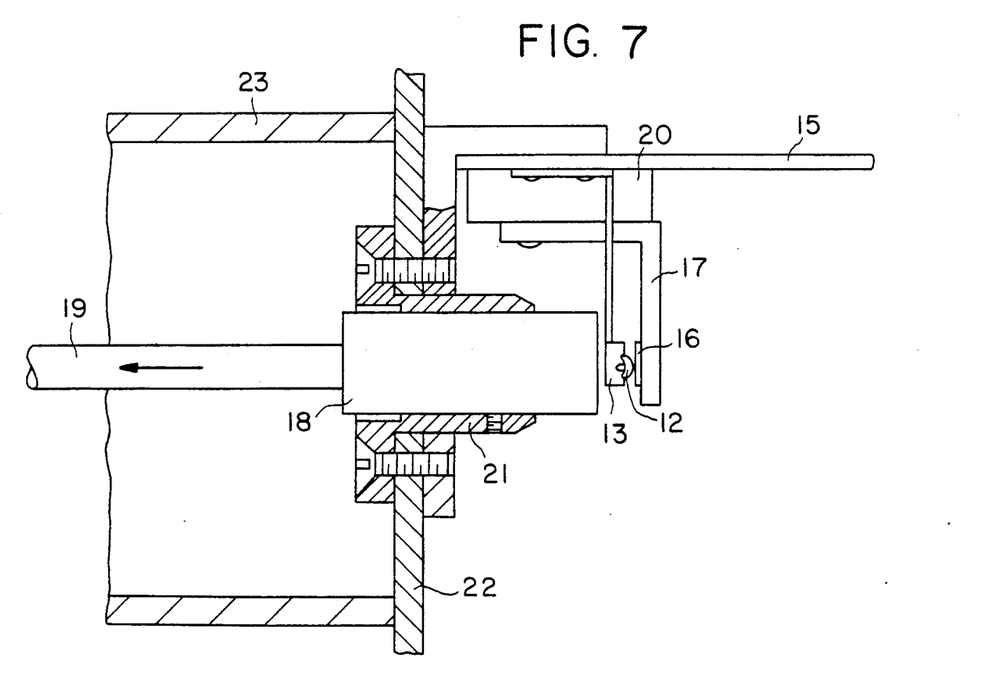
FIG. 7 shows a cross-section of the light source of FIG. 6

Whilst it is possible in the case of the detectors to restrict oneself to items currently available on the market, whereby they are naturally to be selected taking the light source into consideration. It is harder to find suitable light sources since the measuring accuracy and measuring speed attainable depend to a considerable extent on the properties of the light source. Broad spectrum light sources are superior to monochromatic ones in the case of coloured glass vessels since the composition of glass varies greatly due to current recycling practices. FIGS. 6 and 7 and 8 and 9 show two alternative ways of arranging a light source. FIG. 6 shows the inert gas discharge tube 12, for example a xenon lamp, held in clip holding means 13 and 14, which at the same time serve as electrical connections and are linked to the conductor plate 15. A discharge tube of this kind must be ignited by means of high voltage, various solutions being possible. The solution proposed herein comprises an ignition mirror 16, consisting of a conductive material which may be charged with high voltage impulses via a mirror holder 17 with charging means. In so doing, the ignition mirror is not only required to light the lamp, but also to throw light impinging on the mirror back onto a glass fibre end piece 18, from which it is conducted away to a glass fibre conductor 19 following change of the cross-section. An insulation layer 20 is disposed between the mirror holder 17 and the conductor plate 15. The glass fibre end piece 18 is fixed by means of a fitting 21 to the front plate 22 of the housing of the light source. A tube 23 is connected to the front plate 22 in which (see FIG. 3) there is disposed a lens 24 which forms an image of the image diaphragm 25, which is disposed at the end of the glass fibre conductor, on the object being measured. After the lens there is located a double optical wedge 26 with which it is possible to alter the path of the ray, i.e. to focus the image of the image diaphragm on the object being measured. Connected to tube 23 is the above-mentioned shield 11 which is intended to prevent light passing directly from the light source into the detectors. By means of the image diaphragm it is possible to achieve various light patterns on the glass vessels which are adapted in shape and size to said glass vessels, i.e. elongated light bundles for vessel bodies, small spots for narrow openings. By means of the shield it is also possible to swivel the axis of the ray.

Figure 8:
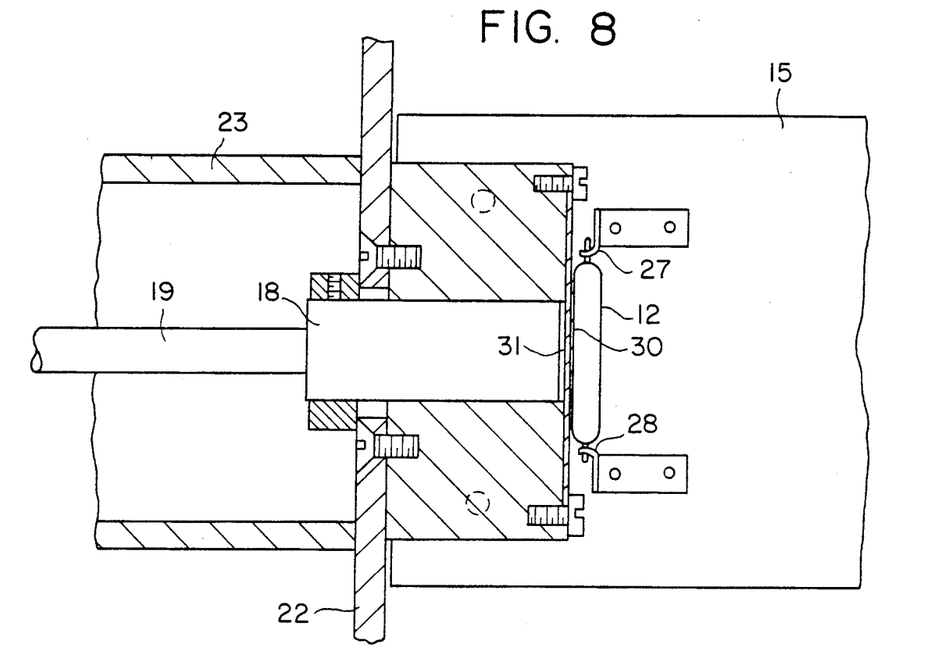
FIGS. 8 and 9 show another embodiment of the light source of FIGS. 6 and 7.
Figure 9:
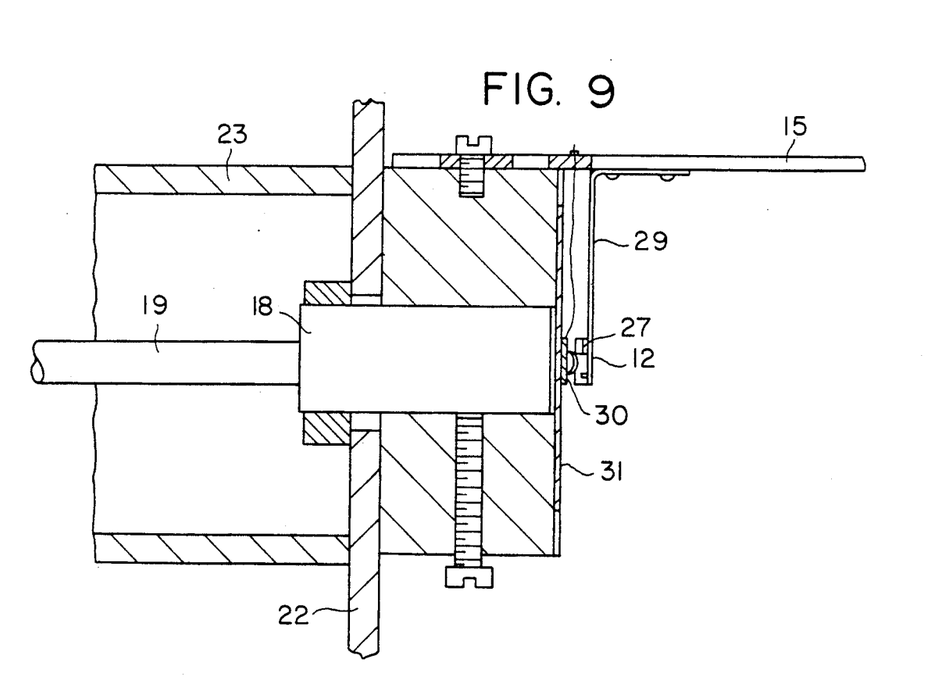

FIGS. 8 and 9 show another embodiment in which an ignition strip is used instead of an ignition mirror. The inert gas discharge tube 12 is held in two clip holding means 27 and 28 which are fixed by means of tensioning pieces 29 to the electrical conductor plate 15 and which serve as electrical contacts. As in the previous example, the lamp is always connected to direct current when in operation and is ignited by means of high voltage impulses. In this embodiment, ignition is achieved by means of an electrically conducting, transparent ignition strip 30. This transparent ignition strip is located on an insulation plate 31 which is generally made of glass and arranged on a holder 32 which holds the glass fibre end piece 18 together with the glass fibre conductor 19.

By using ignition mirrors or ignition strips, a defined light area may be achieved in the xenon lamp with a defined illumination area through the use of glass fibre conductors, light losses may be kept low and furthermore a uniformly illuminated area can be focussed onto the object being measured. The use of optical wedges to deflect the rays onto the object being measured permits the parallel arrangement of several light sources, resulting in an appreciable saving in space compared to previously known arrangements.

The detector groups 9 consist of up to eight detectors 5, which are arranged in a strip. Since as extensive a separation as possible should be aimed at between the individual channels, the shields 10 are important, especially in the case of the detector groups, in order to prevent scattered light and directly impinging light. One conveniently uses photo semiconductor detectors.

Figure 14:
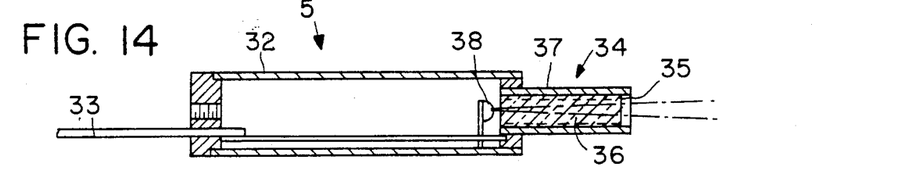
FIGS. 14 and 15 show a cross-section of two further embodiments of detectors.
Figure 15:
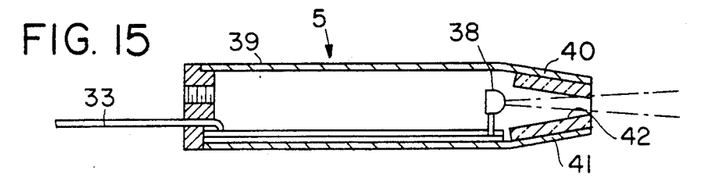

FIGS. 14 and 15 show two preferred embodiments of detectors. In FIG. 14 the detector 5 has a housing 32 from which the leads 33 project on one side and on the other side of which there is fixed an optical arrangement 34 which comprises a diaphragm 35 and, disposed therein, a lens 36. In the present example, the lens 36 is a cylindrical lens, the side surfaces 37 of which are roughened and blackened in order to absorb scattered light. The cylindrical lens focuses the impinging light on the receiver diode 38. This deflector has a higher yield and smaller light scatter than that described earlier.

In FIG. 15 the detector 5 has a housing 39 with, at the forward end i.e. in the area of the diode 38, tapering sides 40 which form a shield 41. The inner surface 42 of the shield is also roughened and blackened.

Figure 16:
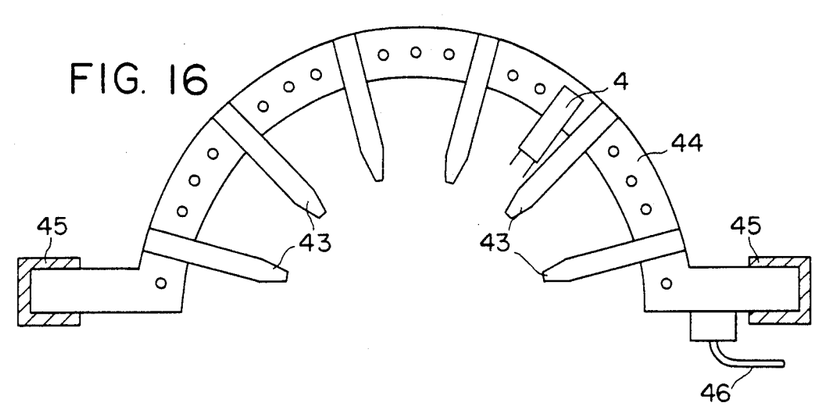
FIG. 16 shows a plan view of an arrangement of detector groups.
Figure 17:
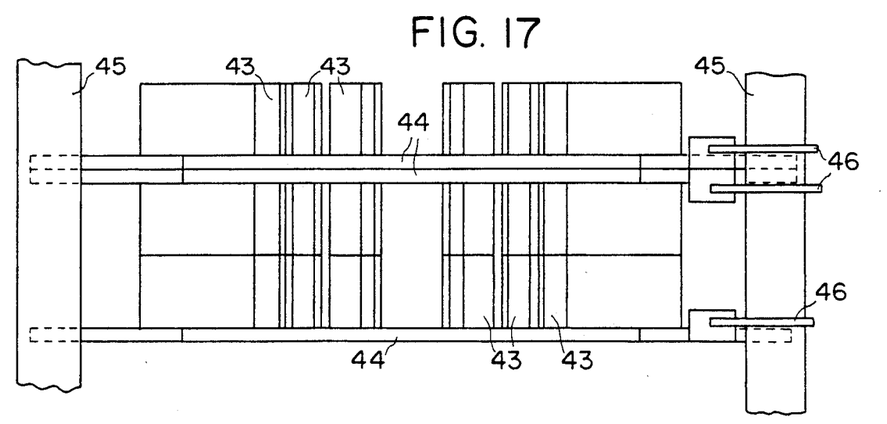
FIG. 17 shows the arrangement of FIG. 16 from the front.

FIG. 16 shows a schematic representation of a possible arrangement of detector groups whereby it follows from the foregoing that the detector groups cover an angle range which is larger vertically and more restricted horizontally. In this figure, six detector groups 43 are arranged rigidly in a semicircular holder 44. The holders forming a semicircle are held in a frame 45 whereby they may be adjusted vertically. The holders have holes 46 into which the light sources 4 may be inserted. FIG. 17 shows three detector arcs, whereby in each case one arc is arranged in inverted manner on the other, facilitating better access to the inside of the arc. This solution has the advantage that for each arc, i.e. for each six detector groups, only one single electrical connection 46 is required which may also include the supply for the light sources, and also that the detector groups may be arranged one on top of the other without gaps.

Figure 3:
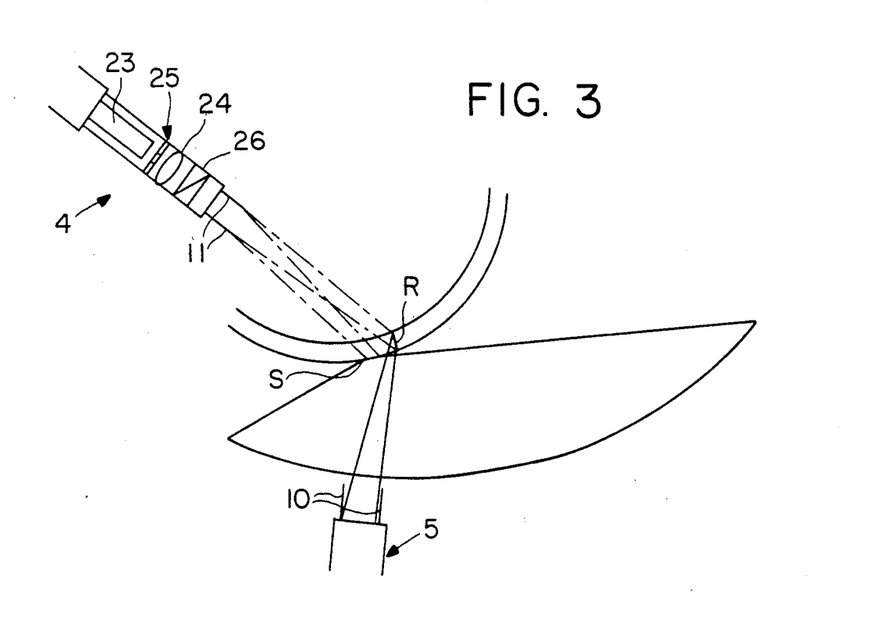
FIG. 3 shows a schematic representation of the path followed by the radiation from transmitter to receiver.

FIG. 3 shows the radiation path of a crack and of a tolerated scatter element. The light coming from the source 4 and projected through the lens 24 onto the object being measured 1 is totally reflected at a crack R and reaches detection element 5. Only a small proportion of the light scattered at a scatter element S reaches the detection element 5 and is not registered by the detection element if the sensitivity level has been correctly set. It follows from the foregoing that better crack detection is achieved if the main beam of totally reflected light from a crack impinges on a detector. However, cracks occur at different angles and since an individual detector can only effectively register small angular cracked areas a large proportion of the cracks are not recognized at all with conventional arrangements, or only indirectly. If the sensitivity of the detector is increased so as to cause some crack locations to respond indirectly, there is a simultaneous increase in the rejection of sound glass vessels. It is therefore necessary to use a larger number of detectors. On the other hand, if a detector covers a larger solid angle than that of the crack ray there is an increase, not only in the scattered light, but also in the useful light. The groups of detectors are therefore to be subdivided into detector elements which are sufficiently small to achieve the maximum ratio between useful light and scattered light.

A number of variants may be employed for the parts of the apparatus hereinbefore described. Thus, it is possible to divert the ray of the light source by means of prisms or mirrors instead of by two wedges and the image diaphragm in front of the glass fibre conductor may be interchangeable in order to produce different image areas on the illuminated glass.

Apart from the inert gas tubes, i.e. the xenon tubes, it is also possible to use other light sources, for example light or laser diodes, lasers or mixed light.

The hereinbefore described radiation source with inert gas discharge tubes as shown in FIGS. 6 to 9 having the switching hereinafter described may, of course, not only be used for crack detection, but also for other lighting problems with optical measuring systems.

Figure 4:
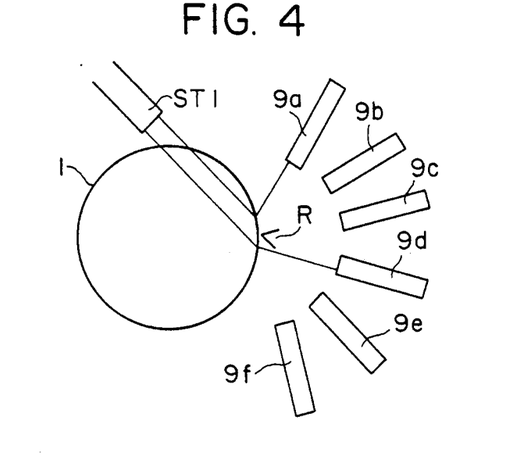
FIGS. 4 and 5 show a measuring station of the apparatus of FIG. 1.
Figure 5:
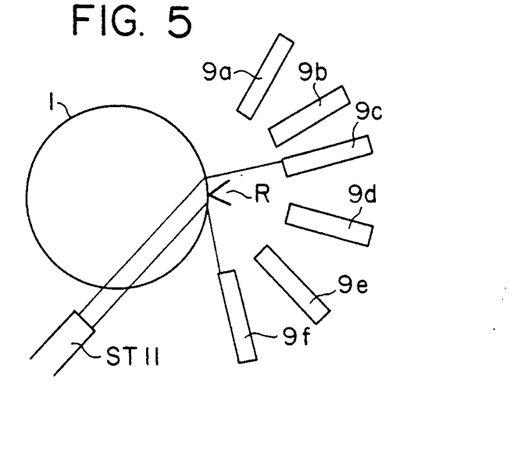

Apart from the hitherto described geometric arrangement of the measuring system, the electronic switching and control of the individual measuring elements also plays an important role as will be explained hereinafter. One of the most important features of electronic switching is the formation of electro-optical channels which are independent of each other. There are 16 of these in the present example. An electro-optical channel is defined here as being a light impulse originating from one or several synchronously switched emitters and detected and registered by from one to all detector groups. In the present example a measuring cycle therefore comprises the emission and detection of 16 lighting impulses. FIGS. 4 and 5 provide a schematic representation of two emitters in two different channels. FIG. 4 shows emitter StI, which could also be a group of emitters, illuminating a crack R whereby the switching electronics, which are explained in more detail below, switch on detector groups 9a to 9d, whilst the two detector groups 9e and 9f are switched off since these receive the direct light from the emitter. Furthermore various levels are set in the detector groups 9a to 9d, for example level 2 for detector groups 9a and 9b, level 3 for detector group 9c and level 5 for detector group 9d. In FIG. 5 another channel is switched on, i.e. emitter II or emitter group II, whereby detector groups 9c to 9f are switched on and detector groups 9a and 9b are switched off. Moreover, in this case, for example, level 6 is set for detector group 9c, level 3 for 9d and level 2 for detector groups 9e and 9f. The switching through of the channels is 25 microseconds. By means of the individual adjustment of the different levels and of the individual conditions of all detector groups in each channel it is possible to achieve a very sharp separation between the channels and an extensive elimination of direct and scattered light. In addition, this enables good adaptation to the problem in hand, i.e. to the nature of the measurement, since a glass vessel has various areas which are examined in different ways. Thus there exist, for example, bottles for mineral water, milk, wine, beer and chemicals; wide-necked containers for preserves, jams and baby food and simple drinking glasses, all of which may be made of brown or green glass. It is necessary here to examine all types of cracks in every angle position and at every point in the vessel as well as surface damage, eruptions, so-called bird-swings, glass splinters, inadequately formed glass and tolerable glass faults such as bubbles or joins.

Figure 11:
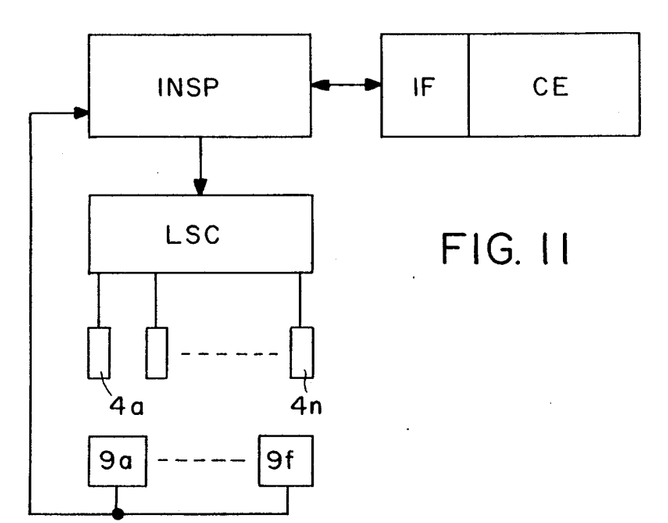
FIG. 11 shows a clock diagram of the measuring arrangement.

FIG. 11 shows a highly simplified diagram of an electronic control system. The control and evaluation unit, CE, equipped with a microprocessor controls, on the one hand, the drive of the various drive parts (not shown here) and, on the other hand, receives signals from the various sensors of the machine. In addition, this unit controls the inspection unit INSP in which, on the one hand, the various operating elements can be shown and, on the other hand, the microprocessor can be programmed. From the inspection unit the signal reaches the light source control LSC which operates the individual light sources 4a to 4n. From the radiated detector groups 9a to 9f the signals reach the inspection unit. Between the control and evaluation unit CE with the microprocessor and the inspection unit INSP there is inserted a memory interface IF in which the entire measuring information from a glass vessel is stored for a time. This is consequently very rapidly accessed from the microprocessor with the result that this latter is able to carry out far more complicated evaluations, such as coincidence criteria, multi-channel conditions or automatic level programming, than if there were no memory interface.

Figure 12:
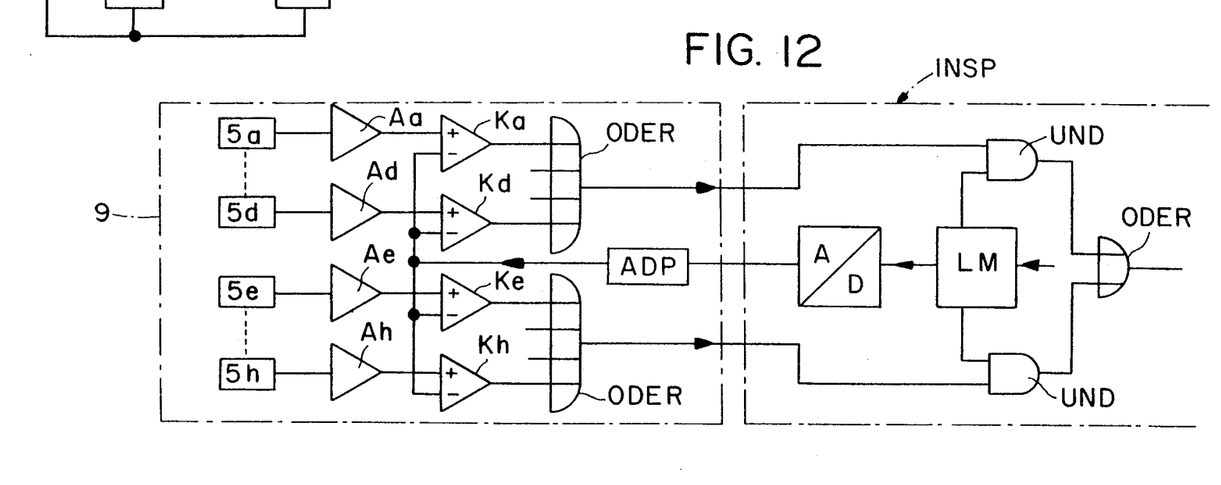
FIG. 12 shows the block diagram of the electronic switching unit of a detector group.

FIG. 12 shows the simplified block diagram of a detector group. Each radiation-sensitive element 5a to 5d and 5e to 5h has its own impulse amplifier Aa to Ad and Ae to Ah with direct current suppression as well as its own comparator Ka to Kd as well as Ke to Kh. The signals from each group of four comparators reach an OR gate. Since it is only the logic exits from the comparators which are linked together, the result being that the portions of scattered light from the elements are not added, as would be the case were one first to add the signals from the elements and then to feed them to the comparator. The two OR gates determine whether a desired display should appear in the upper or lower group of detection elements. From the OR gate the signal reaches an AND gate in which it is compared with a signal from the level memory LM and from there, should both signals be the same, it reaches another OR gate and from there travels for further processing on the apparatus. The level memory LM is a programmable memory into which the levels for the individual detection element groups on the comparators may be entered. From the level store the signal reaches a digital analog converter D/A and from there passes to an adaptor DP and finally to the minus inputs of the comparators. The programming of the level memory is effected from the display panel in accordance with FIG. 10 as will be explained below. Through use of an appropriate microprocessor it is possible to set up a level program for each channel using perfect glass vessels in such a way that only the rejected glass vessels are measured. Thanks to the good reproducibility of the system, the level program may be transferred to other devices. In addition, it is possible to establish statistics for each channel whereby the level program may be manually improved.

Figure 13:
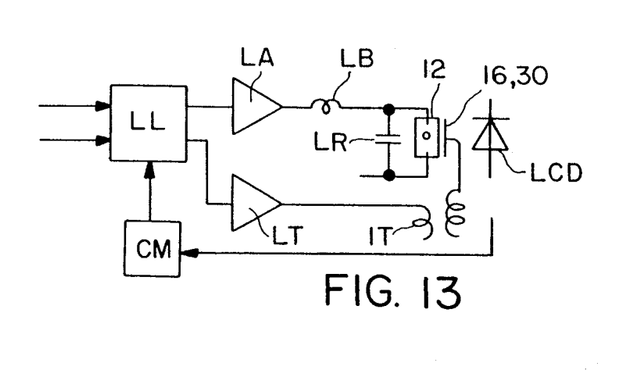
FIG. 13 shows the simplified switching diagram of a flashlight.

FIG. 13 shows the essential features of the light source switching unit. The lamp logic receives impulses from a call-up logic (not shown) and from a synchronization switch unit as well as from a regulator CM and controls supply to the discharge tube 12 via a load load amplifier LA and loading choke LB and also the ignition mirror 16 or the ignition strip 30 via a second load transmitter LT and ignition transformer IT. The light yield of the lamp is measured by a lamp control diode LCD and shown on the control modulator CM which sends a signal to the lamp logic as a function of the light yield, in order to keep the light yield constant.

It will readily apparent to a person skilled in the art that the individual, hereinbefore described switch units may be controlled by a quartz controlled impulse generator, channel counter and selector switch, whereby this control and the programming as well as the control of the various memories and logics lie within the abilities of a person skilled in the art.

Figure 10:
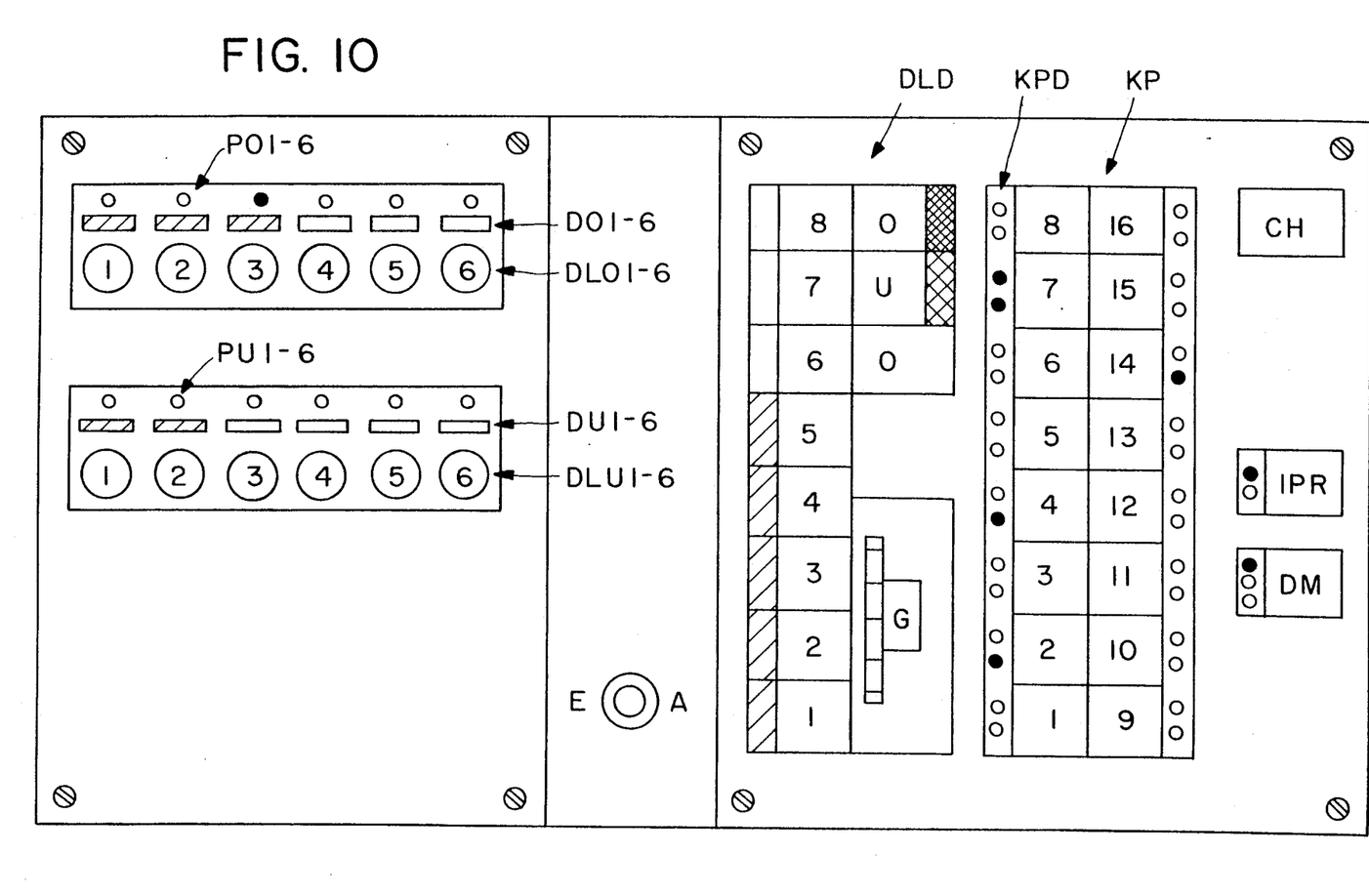
FIG. 10 shows the front panel with the operating elements of the control unit for the apparatus of the instant invention.

FIG. 10 shows the essential display and switching elements of an embodiment of the front panel of the electronic control device. On the left hand side of the front panel there are to be found the display elements and control key for each of six groups of detectors on two levels. All of the display of these elements as well as the possibilities for programming refer in each case to one of the sixteen channels, which can be chosen with another display as will be hereinafter described. The upper round display elements PO 1-5 and PO 1-6 show which group of detectors has been chosen in order to adjust the level. In the present case group 3 of the upper level is under consideration so the display lamp PO 3 is illuminated. The middle rectangular display elements DO 1-6 and DU 1-6 indicate which groups of detectors in a given channel indicate a crack. In the present case display elements DO 1, 2, 3 and DU 1 and 22 are indicating that in these groups of detectors cracks have been detected. The lower keyboard DLO 1-6 and DLU 1-6 enable the programming of the sensitivity level of the individual groups of detectors. In the present case, as mentioned above, by pressing the key DLO3 the level of this group of detectors can be set. This level is optically shown on the adjacent display board DLD where the level is sub-divided into eight stages. It can be seen in the present case that the upper group of detectors 3 is currently set at level 5 and that this setting applies both to the upper "o" as well as to the lower "u" half of the group of detectors. Use of the key O deletes the level for the corresponding group of detectors. The level steps are not programmed in a linear manner, but rather logarithmically whereby a safety margin for the detection of cracks is achieved. Adjacent the detector level display field is situated a programmable glass type switch G which enables the different types of glass to be taken into consideration when programming the level. Next to it is to be found the display and control-fields for the channel programming KP, in which on the one had is shown in which channel work was last carried out and in which given channel display and programming may be chosen. Each channel 1 to 16 has a sequentially numbered key and two channel displays KPD, whereby the lower lamp shows in which channel work is taking place, that is corresponding to a detector group and this upper lamp gives the channel chosen, in this case channel 7. In addition, a total cracks display CH is present, which indicates whether any cracks at all have been found for a given measured object, and which is linked to a guidance system to guide the objects measured with or without cracks onto the appropriate conveyor belt. The display board also contains a further number of display and control elements including for example an on-off switch EA, a display and control field IPR which shows which part of the measuring cycle is in operation, that is whether the inspection cycle, as shown in the drawing, is running or whether the display values have been deleted, the lower lamp in order to measure the next bottle. The control key also renders it possible to shut off the automatic running and to switch over to hand operation. Using the lower field DM the display mode can be shown and altered, for example whether or not each channel is shown after the other or whether a given channel remains on the display or whether or not a given value which is not specific to one channel should be displayed.

In addition still further display elements and counters can be included in the apparatus which are in particular important for statistical purposes. Thus for example it is useful if each channel has a counter, for the number of cracks and flaws per channel to be given and for conclusions to be drawn, at which placed especially large or few number of cracks and other faults occur. The microprocessor thus makes it for example possible to oversee the current failure rate for a channel, or shape and the total and where a net limit is exceeded to trigger an alarm and/or to turn off the installations.

In order to set the optical installation in particular the light sources and to allocate given a light source or light sources to a given channel, it has been found to be convenient to use a given apparatus part in which visible cracks and faults are present. The main constituent of such an auxiliary device is a screen which is used in place of a group of detectors during the setting up of the measuring head. By means of such an auxiliary device, cracks and similar damaged places can be rendered visible. It is, however, also possible to equip the auxiliary device with its own independent auxiliary testing device, whereby it is possible, independently from an automatic testing apparatus, to make certain sample tests relating to testing and initial clarifications in order to ascertain how the entire measuring apparatus should be set up. It is most convenient to chose the size and shape of the screen so that it corresponds to that of a group of detectors and to mark certain detection lines and possibly also scales thereon. The light source fixing means used is conveniently the same as that used in the measuring apparatus.

What is claimed is:

1. An apparatus for detecting by optical means, flaws such as cracks throughout transparent objects, comprising,
   a plurality of radiation sources,
   a plurality of detectors arranged in detector groups disposed around the surface of the transparent object in a vertical strip and having several sensitivity levels, each of the detectors being capable of detecting radiation emitted from a plurality of said radiation sources, the detectors and radiation sources forming independent electro-optical channels,
   detecting means for detecting flaws in the transparent objects through adjustment of the sensitivity levels of each of the detector groups, the sensitivity level of each detector group being able to be independently controlled,
   switching means for switching through a series of independent electro-optical channels sequentially and periodically, each electro-optical channel comprising the emission of an impulse from at least one of said plurality of radiation sources and the detection of the impulse by at least one of said detectors, the switching means including means for adjusting the sensitivity level of each detector after each impulse,
   evaluation means for evaluating the independent electro-optical channels for flaws in the transparent objects through the independently controlled detector groups,
   support means for supporting the radiation sources and detector groups, and
   transport means for transporting the transparent object.

2. An apparatus according to claim 1, whereby the detectors have housings and are provided with means for reducing scattered light.

3. An apparatus according to claim 2, whereby said means for reducing the scattered light are shields mounted on the detector housings.

4. An apparatus according to claim 2, wherein the said means for reducing scattered light in the detectors are roughened, blackened surfaces within the detectors.

5. An apparatus according to claim 1, wherein the detector is provided with a lens and a receiving diode, in particular a cylindrical lens, which focuses light from the radiation source on the receiving diode.

6. An apparatus according to claim 5, wherein the cylindrical lens has roughened and blackened sides.

7. An apparatus according to claim 1, wherein the radiation sources are each provided with an optical system, said optical system comprising a glass fibre end piece having a variable cross-section leading into a glass fibre conductor, a shielding tube with a lens arranged therein, an interchangeable image diaphragm, means for deflecting the radiation, and a shield, said radiation sources being disposed parallel to each other on a stand.

8. An apparatus according to claim 7, wherein the deflecting means is a double wedge.

9. An apparatus according to claim 7, wherein the deflecting means is a prism.

10. An apparatus according to claim 7, wherein the deflecting means is a deflecting mirror.

11. An apparatus according to claim 1, wherein the radiation source is an inert gas discharge tube in particular a xenon tube having a filamentary arc.

12. An apparatus according to claim 1, wherein the radiation source comprises a light emitting diode.

13. An apparatus according to claim 1, wherein a plurality of groups of detectors are assembled together in units at given levels which may be adjusted vertically in a grid pattern and horizontally in the direction of the object being measured.

14. An apparatus according to claim 13, whereby the plurality of groups of detectors are arranged in layers in a semicircular holder and each holder is mounted in a vertically adjustable manner in a frame, the frame being a part of the said support means, and each holder having not more than one electrical connection for the detectors and optionally the radiation sources.

15. An apparatus according to claim 1, wherein each group of detectors comprises eight detectors and a switch, each detector being provided with an impulse amplifier having direct current suppression and a comparator, the comparators being grouped in sets of four comparators, each set being connected to an OR gate from which a signal proceeds to an AND gate in which the signal is compared with a level memory, the level memory being programmable and connected via a digital analog converter and an adaptor to the respective comparators.

16. An apparatus according to claim 1, wherein the radiation source comprises a laser diode.

17. An apparatus according to claim 1, wherein the radiation source comprises a laser emitter.

18. An apparatus according to claim 1, wherein the radiation source comprises a mixed light source.

19. An apparatus according to claim 1, further comprising a plurality of sensors for sensing operating conditions, wherein said evaluation means further comprises an electronic control system having an inspection unit and a control and evaluation unit having a microprocessor, whereby the control and evaluation unit receives a signal from the plurality sensors of the apparatus and controls various drive parts of the apparatus as well as the inspection unit, which causes various operating elements of the apparatus to be displayed and which is connected to a radiation source switching control and a detector group switch.

20. An apparatus according to claim 19, wherein a memory interface is positioned between the control and evaluation unit and the inspection unit in which all measuring information of a transparent object can be intermittently stored.

21. An apparatus according to claim 1, further comprising a control unit having a front panel with a display arranged thereon resulting from a given group of detectors, the display comprising display elements for a crack detected in certain groups of detectors, keys for programming several sensitivity levels in the groups of detectors, whereby the display and a channel chosen by an operator are independent from one another, a detector level display board having a delete key, a channel display and programming field in which a given channel is programmed and displayed, and a channel indicator showing which group of detectors flaw conditions prevail.

22. An apparatus according to claim 21, wherein the front panel has a sum total crack display and the control unit has a counter for each channel.

23. An apparatus according to claim 1, wherein each detector group comprises an upper subgroup and a lower subgroup so as to provide the following four possible detection states: no signal, upper subgroup only, lower subgroup only, and both subgroups.

24. An apparatus for detecting by optical means, flaws such as cracks throughout transparent objects, comprising, a plurality of radiation sources, each radiation source including a shielding tube with a lens arranged therein, an interchangeable image diaphragm and a shield, a plurality of detectors arranged in detector groups disposed around the surface of the transparent object in a vertical strip and having several sensitivity levels, the detectors and radiation sources forming independent electro-optical channels, detecting means for detecting flaws in the transparent objects through adjustment of the sensitivity levels of each of the detector groups, the sensitivity level of each detector group being able to be independently controlled, switching means for switching through independent electro-optical channels sequentially and periodically, evaluation means for evaluating the independent electro-optical channels for flaws in the transparent objects through the independently controlled detector groups, support means for supporting the radiation sources and detector groups, and transport means for transporting the transparent object.

* * * * *